(12) United States Patent
Zheng et al.

(10) Patent No.: US 12,305,234 B2
(45) Date of Patent: May 20, 2025

(54) SERUM miRNA MARKERS FOR DIAGNOSING LIVER CANCER AND PREDICTING LIVER CANCER METASTASIS AND DETECTION KIT THEREOF

(71) Applicant: Zhejiang University, Zhejiang (CN)

(72) Inventors: Min Zheng, Zhejiang (CN); Shuangshuang Li, Zhejiang (CN); Guohua Lou, Zhejiang (CN); Linfu Zhou, Zhejiang (CN); Jiajia Shao, Zhejiang (CN)

(73) Assignee: Zhejiang University, Hangzhou (CN)

( * ) Notice: Subject to any disclaimer, the term of this patent is extended or adjusted under 35 U.S.C. 154(b) by 799 days.

(21) Appl. No.: 17/566,669

(22) Filed: Dec. 30, 2021

(65) Prior Publication Data
US 2022/0127684 A1    Apr. 28, 2022

Related U.S. Application Data

(63) Continuation-in-part of application No. PCT/CN2020/099588, filed on Jun. 30, 2020.

(30) Foreign Application Priority Data

May 31, 2020   (CN) .......................... 202010487210.3

(51) Int. Cl.
*C12Q 1/6876* (2018.01)
*C12Q 1/6886* (2018.01)

(52) U.S. Cl.
CPC ......... *C12Q 1/6876* (2013.01); *C12Q 1/6886* (2013.01)

(58) Field of Classification Search
CPC ................ C12Q 1/6876; C12Q 1/6886; C12Q 2600/178; C12Q 2600/158
See application file for complete search history.

(56) References Cited

U.S. PATENT DOCUMENTS 9,096,895 B2 *   8/2015   Busk ................... C12Q 1/6858

FOREIGN PATENT DOCUMENTS

CN    101017140 A  *  8/2007   ............ C07H 21/00
CN    102985558 A      3/2013
(Continued)

OTHER PUBLICATIONS

Wang Y, et al. Serum exosomal microRNAs combined with alpha-fetoprotein as diagnostic markers of hepatocellular carcinoma. Cancer Med. May 2018;7(5):1670-1679. Epub Mar. 23, 2018. (Year: 2018).*

(Continued)

*Primary Examiner* — Aaron A Priest
*Assistant Examiner* — Emma R Hoppe (57) ABSTRACT

The present application belongs to the field of genetic engineering and medical diagnosis, and particularly relates to serum miRNA markers for diagnosing liver cancer and predicting liver cancer metastasis and a detection kit thereof. The present application discloses the research and development and use of a kit containing three blood miRNAs markers related to human liver cancer. The specific markers are serum-derived miR-122-5p, miR-144-3p and miR-451a. According to the present application, the differential miRNAs are used as the core components of the detection kit, and are combined with corresponding internal references to form the detection kit; and through practical detection application in clinical samples, the reaction conditions and reagent ratios of the kit are optimized, the detection parameters are adjusted, and the standardized process of clinical detection and analysis is preliminarily established, and the kit is used for early diagnosis and metastasis risk assessment of liver cancer.

1 Claim, 2 Drawing Sheets

Specification includes a Sequence Listing.

(56) References Cited

FOREIGN PATENT DOCUMENTS

CN 106867974 A * 6/2017 ........... A01K 67/027
WO 2010043114 A1 4/2010

OTHER PUBLICATIONS

Gui J, et al. Serum microRNA characterization identifies miR-885-5p as a potential marker for detecting liver pathologies. Clin Sci (Lond). Mar. 2011; 120(5):183-93 (Year: 2011).*

International search report of PCT Patent Application No. PCT/CN2020/099588 issued on Jan. 16, 2021.

Hiroya Yamada et al., Associations between Circulating MicroRNAs (miR-21, miR-34a, miR-122 and miR-451) and Non-alcoholic Fatty Liver, Clinica Chimica Acta, 2013, pp. 99-103, No. 424.

* cited by examiner

SEQUENCE LISTING

<160> NUMBER OF SEQ ID NOS: 22

<210> SEQ ID NO 1
<211> LENGTH: 19
<212> TYPE: RNA
<213> ORGANISM: Artificial sequence
<220> FEATURE:
<223> OTHER INFORMATION: synthetic miRNA

<400> SEQUENCE: 1
agugugauaa uggcguuug                                            19

<210> SEQ ID NO 2
<211> LENGTH: 19
<212> TYPE: RNA
<213> ORGANISM: Artificial sequence
<220> FEATURE:
<223> OTHER INFORMATION: synthetic miRNA

<400> SEQUENCE: 2
agugugauaa uggcguuug                                            19

<210> SEQ ID NO 3
<211> LENGTH: 18
<212> TYPE: RNA
<213> ORGANISM: Artificial sequence
<220> FEATURE:
<223> OTHER INFORMATION: synthetic miRNA

<400> SEQUENCE: 3
agugugauaa uggcguuu                                             18

<210> SEQ ID NO 4
<211> LENGTH: 18
<212> TYPE: RNA
<213> ORGANISM: Artificial sequence
<220> FEATURE:
<223> OTHER INFORMATION: synthetic miRNA

<400> SEQUENCE: 4
uggagaguga caaucaug                                             18

<210> SEQ ID NO 5
<211> LENGTH: 22
<212> TYPE: RNA
<213> ORGANISM: Artificial sequence
<220> FEATURE:
<223> OTHER INFORMATION: synthetic miRNA

<400> SEQUENCE: 5
uggggagaga cagugguggu ug                                        22

<210> SEQ ID NO 6
<211> LENGTH: 22
<212> TYPE: RNA
<213> ORGANISM: Homo sapiens

<400> SEQUENCE: 6
uggaguguga caauggguguu ug                                       22

<210> SEQ ID NO 7
<211> LENGTH: 20
<212> TYPE: RNA
<213> ORGANISM: Homo sapiens

<400> SEQUENCE: 7

```
uacaguauag augauguacu                                              20

<210> SEQ ID NO 8
<211> LENGTH: 22
<212> TYPE: RNA
<213> ORGANISM: Homo sapiens

<400> SEQUENCE: 8
aaaccguuac cauuacugag uu                                           22

<210> SEQ ID NO 9
<211> LENGTH: 81
<212> TYPE: DNA
<213> ORGANISM: Artificial sequence
<220> FEATURE:
<223> OTHER INFORMATION: Primer

<400> SEQUENCE: 9
cctgaaagac tcgtatcgca gacgatgtct cgtgtctcgg agtgagacca gtgctagctc    60
tgcttaacat cgtccaaaca c                                            81

<210> SEQ ID NO 10
<211> LENGTH: 82
<212> TYPE: DNA
<213> ORGANISM: Artificial sequence
<220> FEATURE:
<223> OTHER INFORMATION: Primer

<400> SEQUENCE: 10
gagtgtcctt gtcctgatgg ctgcgatcgc tagatcctaa ctggcactgc acctcttgca    60
gctgtgtagt gccagagtac at                                           82

<210> SEQ ID NO 11
<211> LENGTH: 81
<212> TYPE: DNA
<213> ORGANISM: Artificial sequence
<220> FEATURE:
<223> OTHER INFORMATION: Primer

<400> SEQUENCE: 11
cctgaaagac tcgtatcgca gacgatgtct cgtgtctcgg agtgagacca gtgctagctc    60
tgcttaacat cgtcaactca g                                            81

<210> SEQ ID NO 12
<211> LENGTH: 18
<212> TYPE: DNA
<213> ORGANISM: Artificial sequence
<220> FEATURE:
<223> OTHER INFORMATION: Primer

<400> SEQUENCE: 12
cctgaatgcg gctaatcc                                                18

<210> SEQ ID NO 13
<211> LENGTH: 19
<212> TYPE: DNA
<213> ORGANISM: Artificial sequence
<220> FEATURE:
<223> OTHER INFORMATION: Primer

<400> SEQUENCE: 13
ctgaaagact cgtatcgca                                               19
```

```
<210> SEQ ID NO 14
<211> LENGTH: 15
<212> TYPE: DNA
<213> ORGANISM: Artificial sequence
<220> FEATURE:
<223> OTHER INFORMATION: Primer

<400> SEQUENCE: 14
tggagtgtga caatg                                                      15

<210> SEQ ID NO 15
<211> LENGTH: 24
<212> TYPE: DNA
<213> ORGANISM: Artificial sequence
<220> FEATURE:
<223> OTHER INFORMATION: Probe

<400> SEQUENCE: 15
ctcactccga gacacgagac atcg                                            24

<210> SEQ ID NO 16
<211> LENGTH: 16
<212> TYPE: DNA
<213> ORGANISM: Artificial sequence
<220> FEATURE:
<223> OTHER INFORMATION: Primer

<400> SEQUENCE: 16
ccttgtcctg atggct                                                     16

<210> SEQ ID NO 17
<211> LENGTH: 17
<212> TYPE: DNA
<213> ORGANISM: Artificial sequence
<220> FEATURE:
<223> OTHER INFORMATION: Primer

<400> SEQUENCE: 17
tacagtatag atgatgt                                                    17

<210> SEQ ID NO 18
<211> LENGTH: 25
<212> TYPE: DNA
<213> ORGANISM: Artificial sequence
<220> FEATURE:
<223> OTHER INFORMATION: Probe

<400> SEQUENCE: 18
atcgctagat cctaactggc actgc                                           25

<210> SEQ ID NO 19
<211> LENGTH: 16
<212> TYPE: DNA
<213> ORGANISM: Artificial sequence
<220> FEATURE:
<223> OTHER INFORMATION: Primer

<400> SEQUENCE: 19
accgttacca ttactg                                                     16

<210> SEQ ID NO 20
<211> LENGTH: 18
<212> TYPE: DNA
<213> ORGANISM: Artificial sequence
<220> FEATURE:
<223> OTHER INFORMATION: Primer
```

```
<400> SEQUENCE: 20
cctgaatgcg gctaatcc                                               18

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
attgtcacca taagcagcca                                             20

<210> SEQ ID NO 22
<211> LENGTH: 23
<212> TYPE: DNA
<213> ORGANISM: Artificial sequence
<220> FEATURE:
<223> OTHER INFORMATION: Probe

<400> SEQUENCE: 22
tgagaccagc actgcacctc gag                                         23
```

SERUM miRNA MARKERS FOR DIAGNOSING LIVER CANCER AND PREDICTING LIVER CANCER METASTASIS AND DETECTION KIT THEREOF

CROSS-REFERENCE TO RELATED APPLICATION

The present application is a Continuation-in-part Application of PCT Application No. PCT/CN2020/099588 filed on Jun. 30, 2020, which claims the benefit of Chinese Patent Application No. 202010487210.3 filed on May 31, 2020. The contents of the above are hereby incorporated by reference in their entirety.

REFERENCE TO SEQUENCE LISTING

A sequence listing is submitted as an ASCII formatted text filed via EFS-Web, with a file name of "Sequence_listing.TXT", a creation date of Dec. 29, 2021, and a size of 4,487 bytes. The sequence Listing filed via EFS-Web is part of the specification and is incorporated in its entirety by reference herein.

FIELD OF THE INVENTION

The present application belongs to the field of genetic engineering and medical diagnosis, and particularly relates to a serum miRNAs marker kit for diagnosing liver cancer and predicting liver cancer metastasis, and more particularly relates to the research and development and assay performance evaluation of the kit, and the use for early diagnosis and metastasis risk evaluation of liver cancer.

BACKGROUND OF THE INVENTION miRNA is a kind of small non-coding RNA, which is generally more than 20 bases in length. In recent years, more and more studies have found that miRNA plays an important role in the occurrence and development of various diseases, including liver cancer. Studies have shown that miRNA assume a vital role in cell proliferation, differentiation, apoptosis and migration. miRNA generally inhibits translation or leads to degradation of target genes by binding to specific sites in the 3'-UTR region of targeted mRNA. miRNA dysregulation can cause abnormal expression of target genes, thus changing cell physiological functions and accelerating the formation of tumor microenvironment, finally leading to various diseases including cancers. miRNA stably exists in various human body fluids, miRNA in serum can be a potential non-invasive tumor biomarker.

According to the latest statistics in 2020, liver cancer is the sixth most common cancer and the third largest cancer-related death disease in the world. According to previous studies, the abnormal expression of miRNAs makes great contribution to the diagnosis of liver cancer. The present application provides a three-index combined diagnostic kit aimed at abnormally expressed miR-122-5p, miR-144-3p and miR-451a, which is more conducive to the practical detection and application of clinical samples, and can be used for early diagnosis and metastasis risk assessment of liver cancer.

SUMMARY OF THE INVENTION

The present application discloses the development and use of a kit containing three blood miRNA markers related to human liver cancer. The specific markers are serum-derived miR-122-5p of SEQ ID NO: 6, miR-144-3p of SEQ ID NO: 7 and miR-451a of SEQ ID NO: 8.

One object of the present application is to provide a reagent for detecting serum miRNA markers, and the specific markers are serum-derived miR-122-5p, miR-144-3p and miR-451a. The new reverse transcription primers and probe primers of serum miRNAs are listed:

| Names | Sequences |
|---|---|
| 122-RT-loop2[a] (SEQ ID NO: 9) | CCTGAAAGACTCGTATCGCAGACGATGTCTCGTGTCTCGG AGTGAGACCAGTGCTAGCTCTGCTTAACATCGTCCAAACAC |
| 144-RT-loop2 (SEQ ID NO: 10) | GAGTGTCCTTGTCCTGATGGCTGCGATCGCTAGATCCTAAC TGGCACTGCACCTCTTGCAGCTGTGTAGTGCCAGAGTACAT |
| 451-RT-loop2 (SEQ ID NO: 11) | CCTGAAAGACTCGTATCGCAGACGATGTCTCGTGTCTCGG AGTGAGACCAGTGCTAGCTCTGCTTAACATCGTCAACTCAG |
| EV-RT-loop2 (SEQ ID NO: 12) | CCTGAATGCGGCTAATCC |
| 122RT-loop-F2[b] (SEQ ID NO: 13) | CTGAAAGACTCGTATCGCA |
| 122RT-loop-R7[c] (SEQ ID NO: 14) | TGGAGTGTGACAATG |
| 122-RTP-HEX[d] (SEQ ID NO: 15) | HEX-CTCACTCCGAGACACGAGACATCG-BHQ1 |
| 144RT-loop-F2 (SEQ ID NO: 16) | CCTTGTCCTGATGGCT |
| 144RT-loop-R10 (SEQ ID NO: 17) | TACAGTATAGATGATGT |
| 144-RTP-FAM (SEQ ID NO: 18) | FAM-ATCGCTAGATCCTAACTGGCACTGC-BHQ1 |

| Names | Sequences |
|---|---|
| 451RT-loop-R6* (SEQ ID NO: 19) | ACCGTTACCATTACTG |
| EV-RT-loop-F# (SEQ ID NO: 20) | CCTGAATGCGGCTAATCC |
| EV-RT-loop-R (SEQ ID NO: 21) | ATTGTCACCATAAGCAGCCA |
| EV-RTP-HEX (SEQ ID NO: 22) | HEX-TGAGACCAGCACTGCACCTCGAG-BHQ2 |

In the above table and following disclosure, HEX (Hexachlorofluorescein) refers to a fluorescent dye commonly used as a reporter in DNA probes.

FAM (Fluorescein) refers to another widely used fluorescent dye in DNA probes.

BHQ (Black Hole Quencher) refers to a dark quencher to suppress the fluorescence of the reporter dye (such as FAM or HEX) when in proximity.

Preferably, the amplification primer is performed using a TAQMAN probe method.

The present application also includes the use of the reagent in diagnosing liver cancer and predicting liver cancer metastasis.

In addition, the present application also provides a kit for diagnosing human liver cancer and predicting liver cancer metastasis, which comprises reagents for detecting serum miRNA markers, i.e., serum-derived miR-122-5p, miR-144-3p and miR-451a. The reagent comprises reverse transcription primers and amplification primers used in QPCR experiment; the amplification is performed using a TAQMAN probe method.

The present application also includes the use of the kit in diagnosing liver cancer and predicting liver cancer metastasis.

The present application also provides research, development and optimization in the diagnostic kit of the above serum miRNAs markers.

Specifically, the technical solution for solving the technical problems of the present application includes:
1. research of the kit,
2. evaluation of the analytical performance of the kit,
3. use of the kit to detect the target miRNAs in the sample population.

1. Research of the Kit

The specific implementation solution is as follows:

[Test Principle] This kit uses two-step reverse transcription polymerase chain reaction method to detect miR-122-5p, miR-144-3p and miR-451a in human serum. Firstly, miRNAs are reversely transcribed using long primers with stem-loop, and then the cDNA obtained after the reverse transcription is used as a template for PCR amplification.

[Main Components]

TABLE 1

List of Main Components of a Detection Kit Containing Three miRNAs

| Serial numbers | Labels | Components | Quantity (25 detection/pack) |
|---|---|---|---|
| 1 | Reverse transcription buffer solution | Containing deoxynucleoside triphosphate, magnesium ion, reverse transcriptase, etc | 1 tube (400 μL/tube) |
| 2 | Reverse transcription primer 1 | Containing reverse transcription primer of miR-122-5p | 1 tube (60 μL/tube) |
| 3 | Reverse transcription primer 2 | Containing reverse transcription primer of miR-144-3p | 1 tube (60 μL/tube) |
| 4 | Reverse transcription primer 3 | Containing reverse transcription primer of miR-451a | 1 tube (60 μL/tube) |
| 5 | Reverse transcription primer 4 | Containing reverse transcription primer of an internal standard substance | 1 tube (60 μL/tube) |
| 6 | PCR detection buffer | Containing deoxynucleoside triphosphate, magnesium ion, DNA polymerase, etc. | 2 tube (900 μL/tube) |
| 7 | Primer probe 1 | Containing solution of specific miR-122-5p primer and probe | 1 tube (200 μL/tube) |
| 8 | Primer probe 2 | Containing solution of specific miR-144-3p primer and probe | 1 tube (200 μL/tube) |
| 9 | Primer probe 3 | Containing solution of specific miR-451a primer and probe | 1 tube (200 μL/tube) |
| 10 | Primer probe 4 | Containing solution of specific internal standard primer and probe | 1 tube (200 μL/tube) |
| 11 | Positive quality control product | Containing solution of miR-122-5p, miR-144-3p and miR-451a | 1 tube (200 μL/tube) |
| 12 | Internal standard substance | Containing internal standard RNA solution transcribed in vitro | 1 tube (160 μL/tube) |

[Applicable Instrument]

This kit is suitable for ABI7500 real-time fluorescence quantitative PCR instrument.

[Requirements for Samples]

Collecting 2 mL of peripheral blood with a disposable syringe (the blood collection time is usually in the morning or in the forenoon), quickly transfer it into an EDTA anticoagulation tube or a biochemical tube, and evenly mixing. Performing centrifuge for 10 minutes at 3000 rpm and 4° C. within 2 hours, taking the supernatant, and continuing centrifugation at 16000 g at 4° C. for 10 minutes, transfer the supernatant into a new centrifuge tube, and storing it at −80° C. for use.

Note: For the separated serum samples, in order to prevent evaporation of water in the serum samples, the serum samples should be moved into test tubes with stoppers. And if the serum samples can't be detected in time, they should be stored in refrigerator for preservation.

[Detection Method]

1 Preparation of an Amplification Reagent (Preparation Period Before PCR)

Extracting miRNAs in human serum according to the instructions of miRNAs nucleic acid extraction kit selected by users. During extraction, an internal standard is added in the step of cytolysis in an amount of 5 μL/sample. The types of samples to be processed include:

1.1 Clinical samples: clinical samples to be detected;
1.2 Positive quality control products: positive quality control products in the kit.

2 Reverse Transcription 2.1 Preparation of Amplification Reagent (PCR Room I)

Taking out the detection buffer and primers from the kit, melting them on ice or at 2-8° C., shaking all components slightly for even mixing, and centrifuge them briefly at low speed. For each reaction, a reaction system is prepared according to the following ratio:

TABLE 2

System for reverse transcription reaction of the kit

| | | |
|---|---|---|
| Reverse transcription reaction 1 | Reverse transcription buffer solution 3 μL | Reverse transcription primer 1 2 μL |
| Reverse transcription reaction 2 | Reverse transcription buffer solution 3 μL | Reverse transcription primer 2 2 μL |
| Reverse transcription reaction 3 | Reverse transcription buffer solution 3 μL | Reverse transcription primer 3 2 μL |
| Reverse transcription reaction 4 | Reverse transcription buffer solution 3 μL | Reverse transcription primer 4 2 μL |

Calculating the usage amount of each reagent (that is, the total number of people for each reverse transcription reaction solution should include: the number of clinical samples, one tube of positive quality control products and one PCR negative control; the total amount of each reverse transcription reaction solution=number of people*reverse transcription reaction system), adding the reagents into a centrifuge tube with appropriate volume, evenly mixing, and centrifuging briefly. After the reaction solution is prepared, sub-packaging the reaction solution by adding 5 μL of reaction solution into each reverse transcription reaction well, and transferring to a PCR II room after the sub-package.

2.2 Sample Addition (PCR Room II)

Adding the nucleic acid prepared in the step of "1 preparation of amplification reagent (preparation period before PCR)" into the reaction well containing the reverse transcription reaction solution, and the addition amount of each nucleic acid is 5.0 μL/well, and no sample or nucleic acid is added to the negative control well of PCR.

2.3 Reverse Transcription Reaction (Detection Area)

Placing the reaction tube into a fluorescence PCR detector, and setting the circulation parameters as follows:

TABLE 3

Steps of reverse transcription reaction of the kit

| Steps | Number of circles | Temperature (° C.) | Reaction time (min:sec) |
|---|---|---|---|
| 1 | 1 | 42 | 15:00 |
| 2 | 1 | 85 | 00:05 |
| 3 | 1 | 4 | ∞ |

3 PCR Detection 3.1 Preparation of Amplification Reagent (PCR Room I)

Taking out the detection buffer and primer probe from the kit, melting them on ice or at 2-8° C., shaking all the components slightly for mixing them evenly, and performing centrifuge briefly at low speed. For each reaction, a reaction system is prepared according to the following ratios:

TABLE 4 qPCR reaction system of the kit

| | | |
|---|---|---|
| qPCR reaction reagent 1 | PCR detection buffer solution 13 μL | Primer probe 1 7 μL |
| qPCR reaction reagent 2 | PCR detection buffer solution 13 μL | Primer probe 2 7 μL |
| qPCR reaction reagent 3 | PCR detection buffer solution 13 μL | Primer probe 3 7 μL |
| qPCR reaction reagent 4 | PCR detection buffer solution 13 μL | Primer probe 4 7 μL |

Calculating the usage amount of each reagent (that is, the total number of people for each reverse transcription reaction solution should include: the number of clinical samples, one tube of positive quality control products and one PCR negative control; the total amount of each qPCR reaction solution=number of people*qPCR reaction system), adding the reagent into a centrifuge tube with appropriate volume, evenly mixing, and centrifuging briefly. After the reaction solution is prepared, sub-packaging the PCR reaction solution by adding 20 μL of reaction solution into each polymerase chain reaction well, and transferring to a PCR II room after the sub-package.

3.2 Sample Addition (PCR Room II)

Adding the reverse transcription products 1, 2, 3, and 4 of the step 2 in an amount of 5.0 μL/well into reaction wells containing qPCR reaction reagents 1, 2, 3, and 4, respectively.

3.3 PCR Reaction (Detection Area)

Placing the reaction tube into the fluorescence PCR detector, and setting the circulation parameters as follows:

TABLE 5

Steps of PCR reaction of the kit

| Steps | Number of cycles | Temperature (° C.) | Reaction time (min:sec) |
|---|---|---|---|
| 1 | 1 | 95 | 02:00 |
| 2 | 40 | 94 | 00:10 |
|   |   | 57 | 00:40 |

The fluorescence signals are collected at FAM, HEX and CY5 (a cyanine dye), and the data is collected at 57° C. When using ABI7500 instrument, the "Quencher" is set as "none", and "passive reference" is selected as "none".

Explanation of Detection Results

After the reaction, the instrument automatically saves the results. After analyzing the images, adjusting the Start value, End value and Threshold value of Baseline (self-adjustable, the Start value can be between 3-15 and the End value is between 5-20), and adjusting the amplification curve of the PCR negative control.

The Ct value of the PCR negative control should be: HEX (122) of qPCR reaction 1>33.73; FAM (144) of qPCR reaction 2>36.50; HEX (451) of qPCR reaction 3>34.10; and the fluorescence Ct values of FAM and HEX of positive quality control products are ≤31 00.

The above conditions need to be met at the same time in the same experiment, otherwise, the PCR reaction is considered invalid and a new test is required. The details are as follows:

TABLE 6

Determination Results of PCR Reaction of the Kit

| Reaction serial numbers | Fluorescent channels | Ct values | Determination results |
|---|---|---|---|
| qPCR reaction 1 | HEX | Ct ≤ 33.73 | miR122 positive |
|   |   | Ct > 33.73 | miR122 negative |
| qPCR reaction 2 | FAM | Ct ≤ 36.50 | miR144 positive |
|   |   | Ct > 36.50 | miR144 negative |
| qPCR reaction 3 | HEX | Ct ≤ 34.10 | miR451 positive |
|   |   | Ct > 34.10 | miR451 negative |

2. Evaluation of Analysis Performance of the Kit

The specific implementation solution is as follows:
The analytical performance of the kit is mainly evaluated from three aspects of sensitivity, specificity and precision.

1. Sensitivity

The kit is used for qualitative detection of three miRNAs (miR-122-5p, miR-144-3p, miR-451a) in human serum samples. The experimental solution and results of the sensitivity test are as follows.

1.1 Experimental Solution

Synthetic RNA fragments were used for simulation test. Three RNA dry powders (2.5 nmol/tube) of synthetic miR-122-5p, miR-144-3p and miR-451a were dissolved into 1E13 copies/μL nucleic acid solution with 150 μL sterile RNase-free water, which was used as stock solution for subsequent dilution. Three concentrations were selected for sensitivity test, as shown in Table 7. Each miRNA was repeatedly detected 20 times, and the concentration level with more than a positive detection rate of 90% was regarded as the lowest detection concentration. The ABI7500 real-time fluorescence quantitative PCR instrument was used for detection.

TABLE 7

Information of RNA Used in the Lowest Detection Limit Experiment

| Names of miRNAs | Dilution ratio | RNA fragment concentration (copies/μL) |
|---|---|---|
| miR-122-5p | $10^9$ | $10^4$ |
|   | $2 \times 10^9$ | $5 \times 10^3$ |
|   | $4 \times 10^9$ | $2.5 \times 10^3$ |
| miR-144-3p | $10^8$ | $10^5$ |
|   | $2 \times 10^8$ | $5 \times 10^4$ |
|   | $4 \times 10^8$ | $2.5 \times 10^4$ |
| miR-451a | $10^9$ | $10^4$ |
|   | $2 \times 10^9$ | $5 \times 10^3$ |
|   | $4 \times 10^9$ | $2.5 \times 10^3$ |

1.2 Results and Analysis

The detection results are shown in Table 8 and Table 9, illustrating that the positive detection rates of the first two concentrations of the three miRNAs are greater than 90%, the positive detection rate of the third concentration is less than 20%, so the lowest detection concentrations of this kit are $5 \times 10^3$ copies/μL for miR-122-5p, $5 \times 10^4$ copies/μL for miR-144-3p and $5 \times 10^3$ copies/μL for miR-451a. The ABI7500 real-time fluorescence quantitative PCR instrument was used in the experiment.

TABLE 8

Experimental Results of the Lowest Detection Concentration of miR-122-5p

| | miRNAs RNA concentration (copies/μL) miR-122-5p | | |
|---|---|---|---|
| Serial number | $10^4$ Ct/HEX | $5 \times 10^3$ Ct/HEX | $2.5 \times 10^3$ Ct/HEX |
| 1 | 31.03 | 33.5 | 33.73 |
| 2 | 31.31 | 33.18 | 33.67 |
| 3 | 31.21 | 33.39 | 34.29 |
| 4 | 31.45 | 33.73 | 33.6 |
| 5 | 31.63 | 33.23 | 33.94 |
| 6 | 31.69 | 32.39 | 34.49 |
| 7 | 31.58 | 32.97 | 34.15 |
| 8 | 31.27 | 32.79 | 34.11 |
| 9 | 31.11 | 32.87 | 33.96 |
| 10 | 31.4 | 33.1 | 33.77 |
| 11 | 31.21 | 32.99 | 34.26 |
| 12 | 31.06 | 33.37 | 34.15 |
| 13 | 31.15 | 31.75 | 34.03 |
| 14 | 31.19 | 33.39 | 34.45 |
| 15 | 31.5 | 34.48 | 34.26 |
| 16 | 31.41 | 33.4 | 34.34 |
| 17 | 31.38 | 32.98 | 34.48 |
| 18 | 31.37 | 33.29 | 34.79 |
| 19 | 31.11 | 33.25 | 34.75 |
| 20 | 31.74 | 32.91 | 34.41 |
| Averages | 31.34 | 33.15 | 34.18 |
| Positive detection rate | 100% | 95% | 15% |

TABLE 9

Experimental Results of the Lowest Detection Concentrations of miR-144-3p and miR-451a

| | miRNAs | | | | | |
|---|---|---|---|---|---|---|
| | miR-144-3p | | | miR-451a | | |
| | RNA concentrations (copies/μL) | | | | | |
| Serial numbers | $10^5$ Ct/FAM | $5 \times 10^4$ Ct/FAM | $2.5 \times 10^4$ Ct/FAM | $10^4$ Ct/HEX | $5 \times 10^3$ Ct/HEX | $2.5 \times 10^3$ Ct/HEX |
| 1 | 31.79 | 34.42 | 37.02 | 30.96 | 34.06 | 35.46 |
| 2 | 31.32 | 34.33 | 36.69 | 31.05 | 33.21 | 33.99 |
| 3 | 31.04 | 34.19 | 36.07 | 31.18 | 34.09 | 34.79 |
| 4 | 31.38 | 34.11 | 36.83 | 30.78 | 33.79 | 35.07 |
| 5 | 31.47 | 34.53 | 36.67 | 31.24 | 33.14 | 35.69 |
| 6 | 30.93 | 34.14 | 36.97 | 31 | 33.3 | 36.14 |
| 7 | 31.06 | 34.09 | 38.04 | 30.84 | 33.51 | 35.33 |
| 8 | 31.1 | 34.85 | 37.33 | 30.98 | 33.65 | 35.4 |
| 9 | 31.29 | 33.77 | 36.98 | 30.98 | 33.31 | 36.64 |
| 10 | 30.9 | 33.69 | 37.18 | 30.8 | 33.17 | 36.29 |
| 11 | 30.8 | 33.87 | 37.1 | 30.38 | 33.78 | 35.37 |
| 12 | 31.17 | 34.21 | 36.93 | 31.02 | 34.02 | 33.97 |
| 13 | 31 | 34.02 | 35.75 | 31.16 | 32.33 | 35.53 |
| 14 | 30.71 | 33.43 | 37.33 | 31.28 | 33.84 | 35.44 |
| 15 | 30.88 | 34.26 | 36.02 | 31.05 | 32.36 | 35.38 |
| 16 | 31.12 | 34.33 | 37.11 | 30.98 | 34 | 36.21 |
| 17 | 31.1 | 34.34 | 37.44 | 31.07 | 34.1 | 36.15 |
| 18 | 31.4 | 34.86 | 35.9 | 31.01 | 34.05 | 37.5 |
| 19 | 31.24 | 33.69 | 37.02 | 31.01 | 33.89 | 35.28 |
| 20 | 30.87 | 34.61 | 36.72 | 31.33 | 33.59 | 35.37 |
| Averages | 31.13 | 34.19 | 36.86 | 31.01 | 33.56 | 35.55 |
| Positive detection rate | 100% | 100% | 20% | 100% | 100% | 10% |

2. Specificity

The specificity of this kit is mainly verified from two aspects: cross-reaction and interfering substances. The specific experimental solution and results are as follows.

2.1 Cross Reaction

2.1.1. Experimental Solution

In this experiment, five synthetic miRNAs (miR-122b (SEQ ID NO: 1), miR-122b-5p (SEQ ID NO: 2), miR-122-3p (SEQ ID NO: 3), miR-514a (SEQ ID NO: 4) and miR-677a (SEQ ID NO: 5)) with similar sequences to miR-122-5p (SEQ ID NO: 6), miR-144-3p (SEQ ID NO: 7) and miR-451a (SEQ ID NO: 8) were selected as detection objects. The ABI7500 real-time fluorescence quantitative PCR instrument was used for detection.

2.1.2 Results and Analysis

The detection results are shown in table 10, showing that the detection results for miR-122b, miR-122b-5p, miR-122-3p, miR-514a and miR-677a with similar sequences to the three miRNAs detected by this kit are each negative. Therefore, this kit has no cross reactions.

TABLE 10

Experimental Results of Cross Reaction

| Names of nucleic acid | Reaction serial numbers | Fluorescent channels | Ct values |
|---|---|---|---|
| miR-122b | qPCR reaction 1 (miR-122-5p) | HEX | No Ct |
| | qPCR reaction 2 (miR-144-3p) | FAM | No Ct |
| | qPCR reaction 3 (miR-451a) | HEX | No Ct |
| miR-122b-5p | qPCR reaction 1 (miR-122-5p) | HEX | No Ct |
| | qPCR reaction 2 (miR-144-3p) | FAM | No Ct |
| | qPCR reaction 3 (miR-451a) | HEX | No Ct |
| miR-122-3p | qPCR reaction 1 (miR-122-5p) | HEX | No Ct |
| | qPCR reaction 2 (miR-144-3p) | FAM | No Ct |
| | qPCR reaction 3 (miR-451a) | HEX | No Ct |
| miR-514a | qPCR reaction 1 (miR-122-5p) | HEX | No Ct |
| | qPCR reaction 2 (miR-144-3p) | FAM | No Ct |
| | qPCR reaction 3 (miR-451a) | HEX | No Ct |
| miR-677a | qPCR reaction 1 (miR-122-5p) | HEX | No Ct |
| | qPCR reaction 2 (miR-144-3p) | FAM | No Ct |
| | qPCR reaction 3 (miR-451a) | HEX | No Ct |

2.2. Interfering Substances

2.2.1. Experimental Solution

The potential interfering substances mainly include free hemoglobin, bilirubin, triglyceride and total immunoglobulin G (IgG). The verification experiment should be conducted under the worst potential conditions, that is, samples with critical concentration levels (267 and 216) should be selected and added interfering substances with the potential maximum concentration related to medical level.

2.2.2 Results and Analysis

The detection results are shown in Table 12, showing that there is no significant difference between the target fluorescence Ct value of the sample with critical concentration level and the sample without interfering substances (control group) (univariate analysis of variance and paired t test $p > 0.05$), that is, the test sample contains the following concentrations of interfering substances does not affect the determination of the detection results of the samples by the kit:

TABLE 11

Interference Substances and Corresponding Concentrations Thereof

| Name of interfering substances | Bilirubin | Free hemoglobin | Triglycerides | Total immunoglobulin G (IgG) |
|---|---|---|---|---|
| Concentrations | 20 mg/L | 2 mg/mL | 1 mg/mL | 25 mg/L |

TABLE 12

Experimental Results of Interfering Substances

|  | miR-122-5p | | miR-144-3p | | miR-451a | |
|---|---|---|---|---|---|---|
| Interfering substances | 267 HEX | 216 HEX | 267 FAM | 216 FAM | 267 HEX | 216 HEX |
| Bilirubin | 29.07 | 28.58 | 34.33 | 33.45 | 32.37 | 31.68 |
| Free hemoglobin | 28.66 | 28.57 | 35.13 | 33.24 | 32.66 | 31.52 |
| Triglycerides | 28.65 | 28.55 | 34.49 | 33.68 | 31.95 | 31.34 |
| IgG | 29.02 | 28.47 | 34.12 | 33.58 | 31.74 | 31.48 |
| Control | 28.59 | 28.38 | 35.23 | 33 | 32 | 31.39 |
| Univariate analysis of variance | | | P > 0.0 (P = 1.000) | | | |

Conclusion: According to the experimental results in 2.1 and 2.2, this kit has good specificity.

3. Precision

Precision refers to the consistency between independent test results under specified conditions.

3.1. Experimental Solution

In this experiment, RNA solutions of miRNAs, i.e., miR-122-5p, miR-144-3p and miR-451a with high and low concentrations were selected respectively, hence a total of six RNA solutions with different concentrations were tested. Each RNA solution was repeatedly tested for 20 times, and the coefficient of variation (CV, %) of the detection result Ct value was calculated, the CV value should be less than 5%. The ABI7500 real-time fluorescence quantitative PCR instrument was used for the detection.

3.2 Results and Analysis

The detection results are shown in Table 13. The results show that each coefficient of variation of Ct values is less than 5% of the six RNA solutions with different concentrations after repeated detection for 20 times.

TABLE 13

Experimental Results of Precision

|  | miR-122 | | miR-144 | | miR-451 | |
|---|---|---|---|---|---|---|
| Names of Samples | High concentration HEX | Low concentration HEX | High concentration FAM | Low concentration FAM | High concentration HEX | Low concentration HEX |
| 1 | 25.44 | 32.41 | 25.08 | 32.34 | 26.76 | 32.66 |
| 2 | 25.42 | 31.74 | 25.82 | 32.16 | 26.31 | 33.05 |
| 3 | 25.50 | 32.09 | 25.80 | 32.33 | 26.69 | 32.91 |
| 4 | 25.57 | 31.96 | 23.70 | 31.90 | 26.77 | 32.31 |
| 5 | 25.49 | 32.20 | 25.74 | 32.18 | 26.59 | 32.20 |
| 6 | 25.31 | 31.92 | 25.58 | 32.23 | 26.47 | 31.86 |
| 7 | 25.17 | 32.27 | 24.51 | 31.70 | 26.49 | 32.03 |
| 8 | 25.19 | 32.33 | 25.56 | 31.38 | 26.50 | 31.97 |
| 9 | 25.12 | 31.46 | 25.73 | 32.47 | 26.29 | 31.77 |
| 10 | 25.45 | 32.64 | 25.80 | 31.80 | 26.51 | 32.67 |
| 11 | 25.10 | 33.59 | 26.43 | 31.98 | 26.45 | 32.59 |
| 12 | 25.47 | 32.09 | 25.67 | 32.70 | 25.96 | 33.02 |
| 13 | 25.42 | 32.02 | 25.26 | 31.87 | 26.73 | 32.29 |
| 14 | 25.31 | 32.78 | 24.59 | 31.96 | 26.32 | 32.04 |
| 15 | 25.35 | 32.26 | 25.53 | 31.69 | 26.46 | 32.21 |
| 16 | 25.01 | 31.81 | 25.34 | 31.51 | 26.36 | 31.51 |
| 17 | 24.90 | 32.18 | 25.41 | 32.01 | 26.29 | 33.89 |
| 18 | 25.19 | 31.44 | 25.25 | 31.36 | 26.44 | 31.74 |
| 19 | 25.26 | 31.28 | 25.17 | 31.66 | 26.23 | 32.40 |

TABLE 13-continued

Experimental Results of Precision

|  | miR-122 | | miR-144 | | miR-451 | |
|---|---|---|---|---|---|---|
| Names of Samples | High concentration HEX | Low concentration HEX | High concentration FAM | Low concentration FAM | High concentration HEX | Low concentration HEX |
| 20 | 25.46 | 31.71 | 25.28 | 31.19 | 26.25 | 32.48 |
| Averages | 25.31 | 32.11 | 25.36 | 31.92 | 26.44 | 32.38 |
| CV | 0.7% | 1.58% | 2.24% | 1.21% | 0.75% | 1.68% |

3.3 Conclusion

The above experimental results show that the kit has good precision.

To sum up, the sensitivity, specificity and precision of this kit meet the standard.

3. Using the Kit to Detect the Target miRNAs in the Sample Population

The specific implementation solution is as follows:

[Experimental Object]

The TAQMAN probe method was used to detect miR-122-5p, miR-144-3p and miR-451a in serum samples, to see if there were differences in the contents of the three miRNAs in each sample.

[Experimental Raw Materials]

TAKARA TAQ DNA polymerase Hot Start Version; MAQMAX MIRVANA Total RNA Isolation Kit; PRIMESCRIPT RT reagent Kit; 122RT-loop2; 144RT-loop2; 451RT-loop2; EV-RT-loop2; 122RT-loop-F2; 122RT-loop-R7; 122-RT P-HEX; 144RT-loop-F2; 144RT-loop-R10; 144-RT P-FAM; 451RT-loop-R6; EV-RT-loop-F; EV-RT-loop-R; EV-RT P-HEX; ddH$_2$O; 1×TE; Mg$^{2+}$(25 mM); dNTP(25 mM).

[Experimental Steps]

According to the instructions of MIRVANA PARIS RNA Isolation Kit (Applied Biosystem p/n AM1556), miRNA in samples were extracted.

1×TE was used to dilute specific reverse transcription primers 122RT-loop2, 144RT-loop2, 451RT-loop2 and EV-RT-loop2 to 2 M, and then the components in PRIMESCRIPT RT reagent Kit were used to prepare a reverse transcription reaction system according to the following table:

| Names of Reagent | Each test/μL |
|---|---|
| 5× PremeScript Buffer | 2 |
| PrimeScript RT Enzyme Mix I | 0.5 |
| Specific reverse transcription primer (122RT-loop2, 144RT-loop2, 451RT-loop2 or EV-RT-loop2) | 0.5 |
| ddH$_2$O | 4 |
| template | 3 |
| Total | 10 |

The reaction procedure is:

| Temperature | Time |
| --- | --- |
| 42° C. | 15 min |
| 85° C. | 5 s |
| 4° C. | ∞ |

3. After the reverse transcription reaction was completed, 1×TE was used to dilute 122RT-loop-F2, 122RT-loop-R7, 122-RT P-HEX, 144RT-loop-F2, 144RT-loop-R10, 144-RT P-FAM, 451RT-loop-R6, EV-RT-loop-F; EV-RT-loop-R; and EV-RT P-HEX to 20 μM, and then components in TAKARA TAQ DNA polymerase Hot Start Version were used to prepare a qPCR reaction system according to the following table:

| miRNA-122 reaction system | Each test/μL |
| --- | --- |
| 10× buffer | 2.5 |
| HS Taq enzyme | 0.4 |
| Mg$^{2+}$ (25 mM) | 2 |
| dNTP (25 mM) | 0.2 |
| 122RT-loop-F2$^a$ | 0.4 |
| 122RT-loop-R7$^b$ | 0.4 |
| 122-RT P-HEX$^c$ | 0.2 |
| ddH$_2$O | 16.9 |
| RT reaction product (template) | 2 |
| Total | 25 |

| miRNA-144 reaction system | Each test/μL |
| --- | --- |
| 10× buffer | 2.5 |
| HS Taq enzyme | 0.4 |
| Mg$^{2+}$ (25 mM) | 2 |
| dNTP (25 mM) | 0.2 |
| 144RT-loop-F2 | 0.4 |
| 144RT-loop-R10 | 0.4 |
| 144-RT P-FAM | 0.2 |
| ddH$_2$O | 16.9 |
| RT reaction product (template) | 2 |
| Total | 25 |

| miRNA-451 reaction system | Each test/μL |
| --- | --- |
| 10× buffer | 2.5 |
| HS Taq enzyme | 0.4 |
| Mg$^{2+}$ (25 mM) | 2 |
| dNTP (25 mM) | 0.2 |
| 122RT-loop-F2* | 0.4 |
| 451RT-loop-R6 | 0.4 |
| 122-RT P-HEX* | 0.2 |
| ddH$_2$O | 16.9 |
| RT reaction product (template) | 2 |
| Total | 25 |

| Internal standard (EV) reaction system # | Each test/μL |
| --- | --- |
| 10× buffer | 2.5 |
| HS Taq enzyme | 0.4 |
| Mg$^{2+}$ (25 mM) | 2 |
| dNTP (25 mM) | 0.2 |
| EV-RT-loop-F | 0.4 |
| EV-RT-loop-R | 0.4 |
| EV-RT P-HEX | 0.2 |
| ddH$_2$O | 16.9 |
| RT reaction product (template) | 2 |
| Total | 25 |

(The suffix F represents an upstream primer, the suffix R represents a downstream primer. a: 122RT-loop-F2 is an upstream primer for detecting miRNA-122-5p, b: 122RT-loop-R7 is a downstream primer for detecting miRNA-122-5p, c: 122-RT P-HEX is a probe for detecting miRNA-122-5p, the suffix P represents a probe, and the letters following P represent a modified fluorescent group, and so on. *: miR-122-5p and miR-451a share upstream primers and probes; #: internal standard is an exogenous internal standard, which is an artificially designed sequence named EV).

The reaction procedure is:

| temperature | Time | Number of cycles |
| --- | --- | --- |
| 95° C. | 2 min | 1 |
| 95° C. | 10 s | 40 |
| 57° C. | 45 s | |
| | Collecting FAM fluorescence and HEX fluorescence at 57° C. | |

Specific sequences of primer and probes:

| Names | Sequences |
| --- | --- |
| 122-RT-loop2$^a$ (SEQ ID NO: 9) | CCTGAAAGACTCGTATCGCAGACGATGTCTCGTGTCTCGG AGTGAGACCAGTGCTAGCTCTGCTTAACATCGTCCAAACAC |
| 144-RT-loop2 (SEQ ID NO: 10) | GAGTGTCCTTGTCCTGATGGCTGCGATCGCTAGATCCTAAC TGGCACTGCACCTCTTGCAGCTGTGTAGTGCCAGAGTACAT |
| 451-RT-loop2 (SEQ ID NO: 11) | CCTGAAAGACTCGTATCGCAGACGATGTCTCGTGTCTCGG AGTGAGACCAGTGCTAGCTCTGCTTAACATCGTCAACTCAG |
| EV-RT-loop2 (SEQ ID NO: 12) | CCTGAATGCGGCTAATCC |
| 122RT-loop-F2$^b$ (SEQ ID NO: 13) | CTGAAAGACTCGTATCGCA |

-continued

| Names | Sequences |
|---|---|
| 122RT-loop-R7[c] (SEQ ID NO: 14) | TGGAGTGTGACAATG |
| 122-RTP-HEX[d] (SEQ ID NO: 15) | HEX-CTCACTCCGAGACACGAGACATCG-BHQ1 |
| 144RT-loop-F2 (SEQ ID NO: 16) | CCTTGTCCTGATGGCT |
| 144RT-loop-R10 (SEQ ID NO: 17) | TACAGTATAGATGATGT |
| 144-RTP-FAM (SEQ ID NO: 18) | FAM-ATCGCTAGATCCTAACTGGCACTGC-BHQ1 |
| 451RT-loop-R6* (SEQ ID NO: 19) | ACCGTTACCATTACTG |
| EV-RT-loop-F[#] (SEQ ID NO: 20) | CCTGAATGCGGCTAATCC |
| EV-RT-loop-R (SEQ ID NO: 21) | ATTGTCACCATAAGCAGCCA |
| EV-RT P-HEX (SEQ ID NO: 22) | HEX-TGAGACCAGCACTGCACCTCGAG-BHQ2 |

(The suffix F represents an upstream primer, suffix R represents a downstream primer.
[a]122-RT-100p2 is a reverse transcription primer for miRNA-122-5p, [b]122RT-loop-F2 is an upstream primer for detecting miRNA-122-5p, [c]122RT-loop-R7 is a downstream primer for detecting miRNA-122-5p, and [d]122-RT P-HEX is a probe for detecting miRNA-122-5p, suffix P represents a probe, letters after p represents a modified fluorescent group, and so on. *miR-122-5p and miR-451a share upstream primers and probes; [#]internal standard is an exogenous internal standard, which is an artificially designed sequence named EV).

The present application discloses the development and use of a kit containing three blood miRNAs markers related to human liver cancer. Specific markers are serum-derived miR-122-5p, miR-144-3p and miR-451a. According to the present application, the differential miRNAs are used as the core components of the detection kit, and are combined with corresponding internal references to form the detection kit; and through practical detection application in clinical samples, the reaction conditions and reagent ratios of the kit are optimized, the detection parameters are adjusted, and the standardized process of clinical detection and analysis is preliminarily established, and the kit is used for early diagnosis and metastasis risk assessment of liver cancer.

The advantages and beneficial effects of the present application are as follows:

1. miRNAs in serum is a new biomarker, which has the advantages of stability, minimal invasion and easy detection, and can greatly improve the sensitivity and specificity of disease diagnosis. Research and successful development of this kind of small molecular biomarker is helpful for the auxiliary diagnosis of liver cancer, and also provides reference for the research of other diseases.

2. The kit for diagnosing the occurrence of human liver cancer by detecting the expression of specific miRNAs is a systematic and comprehensive diagnostic kit, which can be used for the auxiliary diagnosis of liver cancer patients, help predict the metastasis of liver cancer in patients, help doctors to better grasp the patient's condition in clinic and have a better grasp of the trend of the disease development, so that take more targeted and accurate personalized treatment in time.

3. Compared with SYBRGREEN method, using the TAQMAN probe method to detect the miRNAs in serum samples has higher specificity, better repeatability and more reliable results.

4. Compared with the detection of single miRNAs indicator, the diagnostic kit with multiple miRNAs indicators can improve the sensitivity and specificity of the detection results of the kit, and multi-index miRNAs detection can reduce the error of experimental results caused by individual expression differences of single index in samples, and make the results more accurate and credible.

DETAILED DESCRIPTION OF THE EMBODIMENTS

Example 1: Collection of Samples and Collation of Sample Data

The samples were provided by the First Affiliated Hospital of Zhejiang University School of Medicine (all samples were treated in the same way within 2 hours of collection, and the serum was obtained, packed and stored under the same conditions). By sorting out the sample data, the inventor selected 42 eligible patients with primary liver cancer (i.e., without any operation, chemotherapy or drug treatment for liver cancer before collection) and 39 normal people's peripheral blood collected in the same period as the experimental group.

Example 2: Extraction of miRNA Samples

In the specific operation of the present application, MIR-VANA PARIS Kit (Applied Biosystem p/n AM1556) was used to extract total RNA of the samples.

2.1 375 µL of β-mercaptoethanol was added to 2×Denaturing Solution, mixed well and set aside for use; 21 mL absolute ethanol was added to miRNA Wash Solution 1, mixed well, and set aside for use; 40 mL absolute ethanol was added to Wash Solution 2/3, mixed well and set aside for use.

2.2 2×Denaturing-Solution was added to 300 µL serum with the same amount, vortex mixed well and then placed on ice for 5 minutes, and 5 µL exogenous internal standard was added to each sample.

2.3 Phenol/chloroform with the same volume as the total volume was added, and then vortex mixed for 30-60 s and centrifuged at 16000 g for 10 min at room temperature.

2.4 The supernatant was carefully transfered into a new 1.5 mL centrifuge tube, and then added absolute ethanol with 1.25 times the volume, vortex mixed.

2.5 The clean centrifugal column was placed in a clean collecting tube, and the liquid from the previous step was added into the column, and then centrifuged at 10000 g for 30 seconds at room temperature. The flow-through liquid was discarded, and the centrifugal column was placed in the collecting tube again. Repeated this step until all the liquid has passed through the column.

2.6 700 µL of miRNA Wash Solution 1 was added into the centrifugal column, and then centrifuged at 10000 g for 15 seconds at room temperature. The flow-through liquid was discarded, and the centrifugal column was placed in the collecting tube again.

2.7 500 µL of Wash Solution 2/3 was passed through the column twice, and the empty column was centrifuged for 1 minute. Then the centrifugal column was placed in a new collecting tube, and 50 µL of nuclease-free water preheated at 95° C. was added to the center of the column, and then centrifuged at the highest speed for 30 seconds at room temperature. The liquid in the collecting tube was the extracted total RNA, which can be stored at −80° C.

Example 3: Detection of Target MiRNAS in the Samples by the Kit

Samples collected in Example 1 were subjected to QPCR detection of miRNAs 3.1 Reverse transcription reaction: 4 µL of RNase Free dH$_2$O, 2 µL of 5×buffer (PRIMESCRIPT Buffer2), 0.5 µL of specific reverse transcription primers, 0.5 µL of reverse transcriptase (PRIMESCRIPT RT Enzyme Mix I) and 3 µL of sample template were added into the reaction tube, to reach a final volume of 10 µL, then incubated at 42° C. for 15 min, 85° C. for 5 s, and 4° C. for ∞. The obtained cDNA template was stored at −20° C. for use.

3.3 QPCR operation: a 25 µL of reaction system was adopted, and the reaction system was configured as shown in the table. Configuration and loading steps were all carried out on ice. The reaction was suitable for ABI7500 real-time fluorescence quantitative PCR instrument.

Example 4 Analyze the Prediction and Diagnosis of Each miRNAs on the Occurrence and Metastasis of Liver Cancer With miR-122-5p, miR-144-3p and miR-451a as research objects, 42 cases of serum samples from liver cancer patient and 39 cases of serum samples from normal people were detected using the kit, and the predictive diagnosis of liver cancer occurrence and metastasis by miRNAs was analyzed according to the Ct value results, and the sensitivity and specificity of normal group and liver cancer group were compared.

Figure 1:
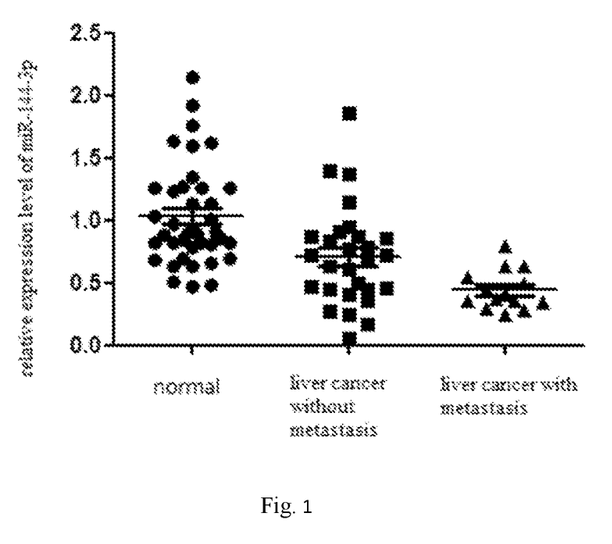
FIG. 1 shows the expression of miR-144-3P in serum detected by the kit in three groups: normal people, liver cancer patients without metastasis and liver cancer patients with metastasis.
Figure 2:
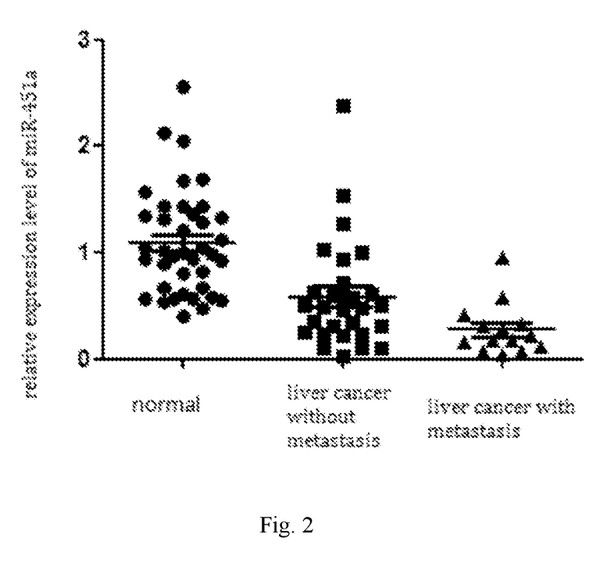
FIG. 2 shows the expression of miR-451a in serum detected by the kit in three groups: normal people, liver cancer patients without metastasis and liver cancer patients with metastasis.
Figure 3:
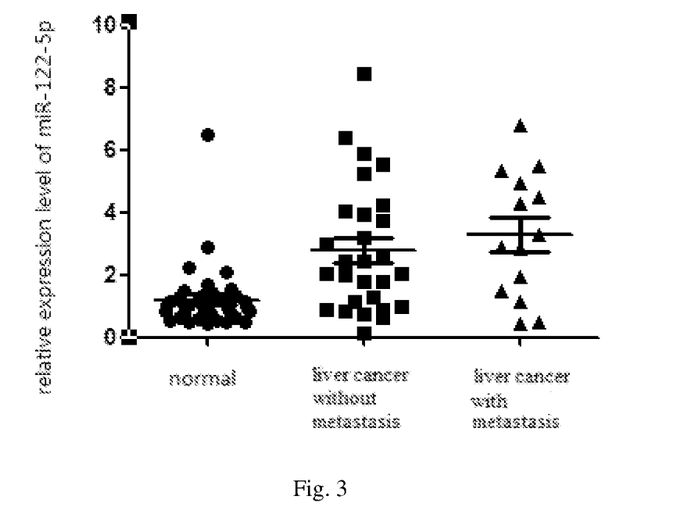
FIG. 3 shows the expression of miR-122-5p in serum detected by the kit in three groups: normal people, liver cancer patients without metastasis and liver cancer patients with metastasis.

Specific results: the experiments showed that the levels of miR-144-3p and miR-451a in the serum of the liver cancer group were significantly lower than those in normal group. The data of liver cancer group were further analyzed, and the patients with liver cancer were divided into two groups: those with metastasis (patients with distant metastasis, intrahepatic metastasis or portal vein tumor thrombus identified by iconography) and those without metastasis. The experimental results showed that the expression of miR-144-3p and miR-451a of liver cancer patients with metastasis was significantly lower than that of liver cancer patients without metastasis, which indicated that these two indexes were related to the malignant degree of liver cancer. While the level of miR-122-5p in the serum of liver cancer group was significantly higher than that of the normal group, but there was no significant difference between the groups with and without metastasis of liver cancer.

Figure 4:
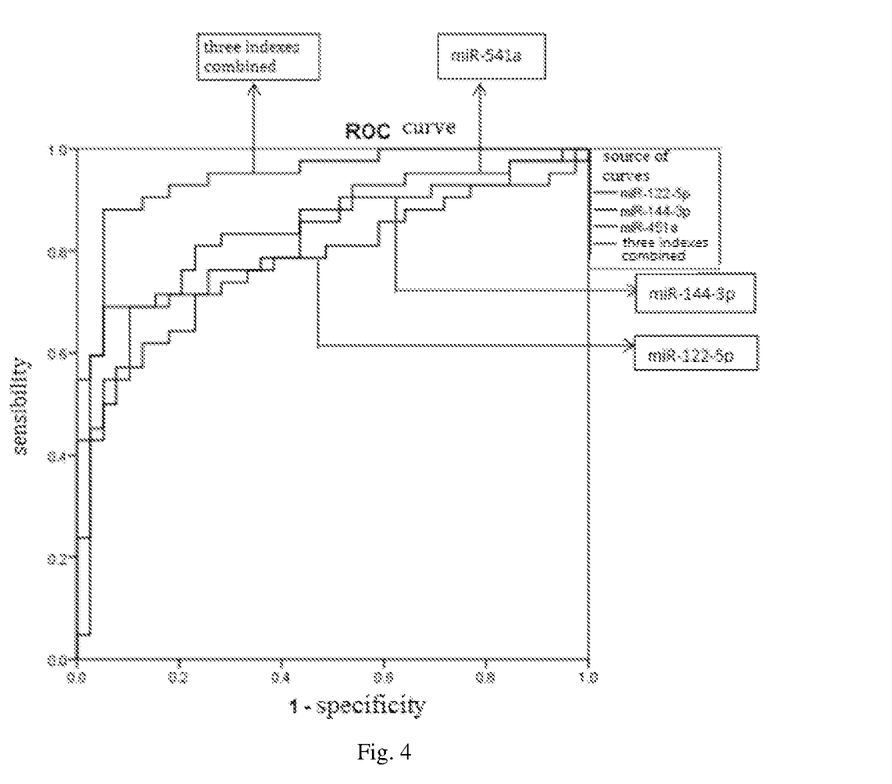
FIG. 4 shows the sensitivity and specificity of detecting and distinguishing the liver cancer group and the normal group with miR-144-3P, miR-451a and miR-122-5p alone and in combination by using ROC curves analysis.

ROC curve analysis showed that the AUC value of miR-122-5p was 0.783 when distinguishing the liver cancer group from the normal group, the AUC value of miR-144-3p is 0.808 when distinguishing the liver cancer group from the normal group, and the AUC value of miR-451a is 0.858 when distinguishing the liver cancer group from the normal group. And the AUC value is 0.938 when the three indexes are combined. The experimental results showed that serum miR-122-5p, miR-144-3p and miR-451a, as biomarkers of liver cancer, have desirable sensitivity and specificity, and the combined diagnosis by these three indicators has a better effect.

| | Area under curve | | | | |
|---|---|---|---|---|---|
| Variables of detection results | Area | Standard error [a] | Asymptotically Sig. [b] | Asymptotic 95% confidence interval | |
| | | | | Lower limit | Upper limit |
| miR-122-5p | .783 | .054 | .000 | .678 | .888 |
| miR-144-3p | .808 | .048 | .000 | .713 | .902 |
| miR-451a | .858 | .042 | .000 | .775 | .940 |
| three indexes combination | .938 | .028 | .000 | .884 | .993 |

[a] under the nonparametric hypothesis
[b] Zero hypothesis: real area = 0.5.

The invention claimed is:

1. A composition comprising the following primers and probes:

| Names | Sequences |
|---|---|
| 122-RT-loop2* (SEQ ID NO: 9) | CCTGAAAGACTCGTATCGCAGACGATGTCTCGTGTCTCGGAGTGAGACCAGTGCTAGCTCTGCTTAACATCGTCCAAACAC |
| 144-RT-loop2 (SEQ ID NO: 10) | GAGTGTCCTTGTCCTGATGGCTGCGATCGCTAGATCCTAACTGGCACTGCACCTCTTGCAGCTGTGTAGTGCCAGAGTACAT |
| 451-RT-loop2 (SEQ ID NO: 11) | CCTGAAAGACTCGTATCGCAGACGATGTCTCGTGTCTCGGAGTGAGACCAGTGCTAGCTCTGCTTAACATCGTCAACTCAG |
| EV-RT-loop2 (SEQ ID NO: 12) | CCTGAATGCGGCTAATCC |
| 122RT-loop-F2[b] (SEQ ID NO: 13) | CTGAAAGACTCGTATCGCA |
| 122RT-loop-R7[c] (SEQ ID NO: 14) | TGGAGTGTGACAATG |
| 122-RT P-HEX[d] (SEQ ID NO: 15) | hexachlorofluorescein-CTCACTCCGAGACACGAGACATCG-dark quencher dye |
| 144RT-loop-F2 (SEQ ID NO: 16) | CCTTGTCCTGATGGCT |
| 144RT-loop-R10 (SEQ ID NO: 17) | TACAGTATAGATGATGT |
| 144-RT P-FAM (SEQ ID NO: 18) | carboxyfluorescein-ATCGCTAGATCCTAACTGGCACTGC-dark quencher dye |
| 451RT-loop-R6* (SEQ ID NO: 19) | ACCGTTACCATTACTG |
| EV-RT-loop-F# (SEQ ID NO: 20) | CCTGAATGCGGCTAATCC |
| EV-RT-loop-R (SEQ ID NO: 21) | ATTGTCACCATAAGCAGCCA |
| EV-RT P-HEX (SEQ ID NO: 22) | hexachlorofluorescein-TGAGACCAGCACTGCACCTCGAG-dark quencher dye. |

* * * * *